(12) United States Patent
Shao

(10) Patent No.: US 9,963,694 B2
(45) Date of Patent: May 8, 2018

(54) WASH SOLUTION AND WASHING METHOD FOR HYBRID-ENRICHMENT-CAPTURE DNA SEQUENCING LIBRARY

(71) Applicant: Yang Shao, Nanjing (CN)

(72) Inventor: Yang Shao, Nanjing (CN)

(73) Assignee: NANJING SHIHE GENE BIOTECHNOLOGY INC., LTD., Nanjing (CN)

( * ) Notice: Subject to any disclaimer, the term of this patent is extended or adjusted under 35 U.S.C. 154(b) by 0 days. days.

(21) Appl. No.: 15/501,963

(22) PCT Filed: Aug. 4, 2015

(86) PCT No.: PCT/CN2015/086012
§ 371 (c)(1),
(2) Date: Feb. 6, 2017

(87) PCT Pub. No.: WO2016/023431
PCT Pub. Date: Feb. 18, 2016

(65) Prior Publication Data
US 2017/0226581 A1 Aug. 10, 2017

(30) Foreign Application Priority Data
Aug. 13, 2014 (CN) .......................... 2014 1 0395399

(51) Int. Cl.
*C12N 15/10* (2006.01)
*C12Q 1/68* (2018.01)
*C40B 40/06* (2006.01)

(52) U.S. Cl.
CPC ........... *C12N 15/10* (2013.01); *C12Q 1/6874* (2013.01); *C12N 15/1006* (2013.01)

(58) Field of Classification Search
CPC ... C12N 15/10; C12N 15/1006; C12Q 1/6874
See application file for complete search history.

(56) References Cited

U.S. PATENT DOCUMENTS

2014/0094384 A1    4/2014 Solomon et al.

FOREIGN PATENT DOCUMENTS

CN    102533727 A    7/2012
CN    104178817 A    12/2014

OTHER PUBLICATIONS

International Search Report (PCT/ISA/210) dated Nov. 26, 2015, by the State Intellectual Property Office of the P.R. China. Patent Office as the International Searching Authority for International Application No. PCT/CN2015/086012.

(Continued)

*Primary Examiner* — Jeremy C Flinders
(74) *Attorney, Agent, or Firm* — Buchanan Ingersoll & Rooney PC

(57) ABSTRACT

This application provides a detailed description of a washing solution consisting of saline sodium citrate (SSC) buffer and sodium dodecyl sulfate (SDS) for hybridization-enrichment-capture DNA sequencing libraries as well as a corresponding washing method. The invented solution has a simple recipe, which is low-cost and easily produced and stored. The washing strategy associated with the invented solution is simple and easy to carry out, requiring no special instruments, and the results produced thereby are outstanding with low background noise, which consequently leads to an improvement on the efficiency of targeted enrichment. Elution of the library after washing is easy to carry out and requires no additional reagents or purification, effectively reducing loss of material due to further purification and time needed for completion of procedure.

2 Claims, 1 Drawing Sheet

(56) References Cited

OTHER PUBLICATIONS

Written Opinion (PCT/ISA/237) dated Nov. 26, 2015, by the State Intellectual Property Office of the P.R. China as the International Searching Authority for International Application No. PCT/CN2015/086012.

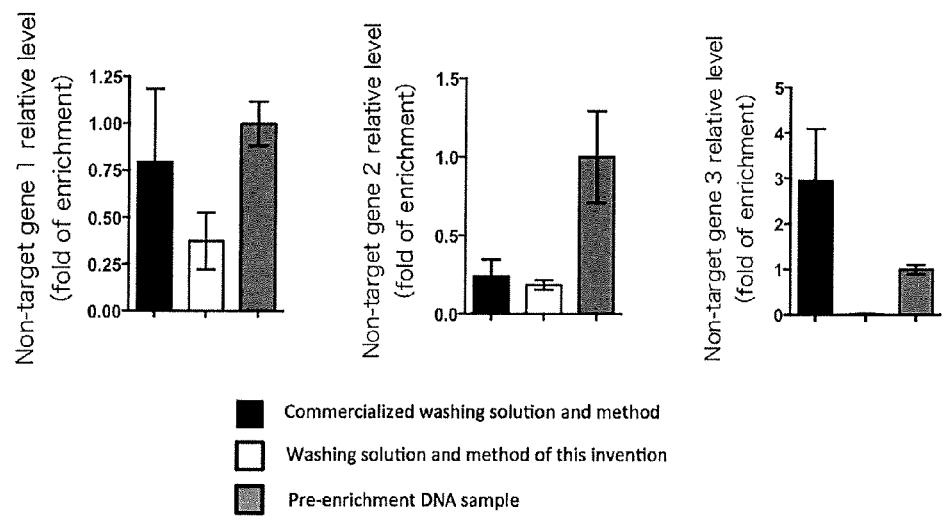

WASH SOLUTION AND WASHING METHOD FOR HYBRID-ENRICHMENT-CAPTURE DNA SEQUENCING LIBRARY

BACKGROUND OF THE INVENTION

Field of the Invention

The present invention relates to a washing solution for hybridization-enrichment-capture DNA sequencing libraries, and a washing method thereof.

Description of Related Art

Double-stranded nucleic acid molecules (e.g. DNA, DNA/RNA, RNA/RNA) exist in double-helix structures. The double-helix structure is stabilized by the hydrogen bonds between complementary bases (e.g. A+T/U or G+C) of two strands and the hydrophobic force for base stacking. Complementary base pairing is the central dogma of all processes involving nucleic acids. In a basic hybridization reaction, nucleic acid probes or primers are designed to be able to complementarily bind with target sequences. Hybridization-enrichment-capture DNA sequencing libraries is one application of such principle for targeted sequencing of particular genomic regions or a particular group of genes.

The efficiency and precision of nucleic acid hybridization depend on three factors: (1) conditions of denaturation (i.e. separation); (2) conditions of renaturation (i.e. reannealing); (3) conditions of post-hybridization washing. Once the complementary strands are separated, primers or probes would bind to target nucleic acids during the "renaturation" step. This step sometimes is also called the "hybridization" step. In the course of hybridization-enrichment-capture of DNA sequencing libraries, biotinylated probes which are hybridized with genomic target sequences would bind closely with streptavidin beads and in turn be captured. Afterwards, all unbound or non-specifically bound DNA sequences would be removed through a series of washing steps. The stringency of these washing steps largely decides the specificity of bonds between target sequences and capture probes. DNA duplexes of high complementarity display greater stability under stringent washing conditions than those of low complementarity. As such, raising the stringency of washing steps would facilitate the removal of non-specifically bound probes and genomic DNA sequences.

The stringency of the washing steps depends on three adjustable factors: 1. Temperature: as temperature rises, non-specifically bound probes and genomic DNA sequences become denatured and separated; 2. Salt concentration: as salt concentration drops, non-specifically bound probes and genomic DNA sequences become denatured and separated; 3. Incubation time: as washing time increases, non-specifically bound probes and genomic DNA sequences become denatured and separated. Other factors such as pH value and number of washing would also affect the stringency of the washing steps.

SUMMARY OF THE INVENTION

An object of the present invention is to provide a washing solution that can be used to wash DNA sequencing libraries enriched by hybridization capture based on the binding of biotin-labeled probes and streptavidin beads in a low-cost, simple, quick and highly efficient manner, and a washing strategy using the aforementioned solution and a method for subsequent elution of the enriched sequencing libraries. To this end, the following technical plan is proposed.

This invention contains a washing solution for DNA sequencing libraries enriched by hybridization capture technology, consisting of saline sodium citrate (SSC) buffer and sodium dodecyl sulfate (SDS), wherein the SSC buffer and SDS are separately packaged.

In one preferred embodiment of the present invention, the SSC buffer consists of NaCl and sodium citrate, with a pH value between 6.8 and 7.2.

The present invention also provides a washing method with the above washing solution provided by the embodiment of this disclosure.

The washing solution adopted includes the following three portions:
washing solution I: 1×SSC, 0.1% SDS;
washing solution II: 0.1×SSC, 0.1% SDS;
washing solution III: 0.2×SSC, 10% SDS.

The washing method comprises the following steps:
(1) for each enrichment reaction, pre-incubating 1 ml washing solution I and 2 ml washing solution II at 65° for 30 minutes, and placing the other two portions under room temperature;
(2) briefly centrifuging a hybridization reaction with biotin-labeled DNA probes captured by Invitrogen Dynabeads® M270 Streptavidin beads in a centrifuge tube at 600×g for 3 seconds, to ensure that there are no beads left on the tube wall or tube lid;
(3) placing the centrifuge tube on a magnetic separation rack and letting it stand for 1 minute until the liquid inside is clear, then carefully removing and discarding the supernatant;
(4) removing the centrifuge tube from magnetic stand and adding 1 ml of washing solution I pre-warmed at 65° in step (1), mixing thoroughly by pipetting up and down for 10 times, and then incubating the mixture at 65° for 5 minutes;
(5) placing the centrifuge tube on the magnetic separation rack and letting it stand for 1 minute until the liquid inside is clear, then carefully removing and discarding the supernatant;
(6) removing the centrifuge tube from magnetic stand and adding 1 ml of washing solution II pre-warmed at 65° in step (1), mixing thoroughly by pipetting up and down for 10 times, and then incubating the mixture at 65° for 5 minutes;
(7) placing the centrifuge tube on the magnetic separation rack and letting it stand for 1 minute until the liquid inside is clear, then carefully removing and discarding the supernatant;
(8) repeat step (6)-(7) for one more time;
(9) removing the centrifuge tube from magnetic stand and adding 1 ml of room temperature washing solution II, mixing thoroughly by pipetting up and down for 10 times, and then placing the centrifuge tube into rotary mixer and spinning it for 5 minutes;
(10) removing the centrifuge tube from magnetic stand and briefly centrifuging it at 600×g for 3 seconds to ensure that no beads are left on the tube wall or tube lid;
(11) placing the centrifuge tube on the magnetic separation rack and letting it stand until the liquid inside is clear, then carefully removing and discarding the supernatant as much as possible with a P10 pipette;
(12) keeping the centrifuge tube on the magnetic rack and adding 1 ml of washing solution III against the tube wall opposite to the beads, counting 30 seconds then carefully removing and discarding the supernatant as much as possible with the pipette;

(13) Letting the beads dry for 2 minutes, adding 22.5 μl nuclease-free water to resuspend magnetic beads by mixing them with the pipette up and down for 10 times, followed by heating the centrifuge tube at 98° for 10 minutes;
(14) after heating, vortex mixing the centrifuge tube and then briefly centrifuging it at 600×g for 3 seconds to ensure that no beads are left on the tube wall or tube lid;
(15) placing the centrifuge tube on the magnetic rack until the liquid inside is clear, immediately removing 20 μl supernatant containing hybridization-capture enriched DNA library sample for subsequent post-enrichment amplification.

The advantages offered by the present invention include:
(1) the washing solution provided is easy to prepare in a cost-effective manner, and the components thereof are easily accessed and stored.
(2) the washing method provided with the above washing solution is easy to carry out, and requires no special instruments.
(3) the present invention produces outstanding washing results with low background noise (as shown in FIG. 1) and an improvement on the efficiency of targeted enrichment (the targeting rate rises from 60% to 85% compared with that of commercialized washing solutions).
(4) the elution step after washing is easy to carry out and requires no additional reagents or steps for purification, thus reducing overall hands-on time and the loss of material due to additional purification step.

BRIEF DESCRIPTION OF THE DRAWINGS

FIG. 1. Histograms demonstrate comparisons between the washing results obtained by using the present invention and the results obtained by using a commercialized solution. Enrichment folds of non-target genes (i.e. background noise) were measured by real-time qPCR. Data was presented with mean±SD from three independent experiments with triplicates in each.

DETAILED DESCRIPTION OF THE INVENTION

The present invention is further defined by reference, but not in any way limited, to the following illustrative example. The illustrative example, which is for a skilled personnel to prepare the washing solution provided by the present invention and to carry out the washing method thereof, describes in detail specific components and ratios thereof, reagents and amounts thereof, solution pH values, experimental conditions, and so on.

Example 1

The preparation of the washing solution for DNA sequencing libraries enriched by hybridization capture is as follows, wherein the solution consist of saline sodium citrate (SSC) buffer and SDS and are capable of long time preservation under 4°.
1) Required reagents: 20×SSC (3M NaCl, 300 mM sodium citrate, with pH value adjusted to 7.0), 10% SDS;
2) Washing solution I: 1×SSC, 0.1% SDS;
3) Washing solution II: 0.1×SSC, 0.1% SDS;
4) Washing solution III: 0.2×SSC, 10% SDS.

The washing method and subsequent elution using the above washing solution are as the following steps:
(1) for each enrichment reaction, pre-incubating 1 ml washing solution I and 2 ml washing solution II at 65° for 30 minutes, and placing the other two portions under room temperature;
(2) briefly centrifuging a hybridization reaction with biotin-labeled DNA probes captured by Invitrogen Dynabeads® M270 Streptavidin beads in a centrifuge tube at 600×g for 3 seconds, to ensure that there are no beads left on the tube wall or tube lid;
(3) placing the centrifuge tube on a magnetic separation rack and letting it stand for 1 minute until the liquid inside is clear, then carefully removing and discarding the supernatant;
(4) removing the centrifuge tube from magnetic stand and adding 1 ml of washing solution I pre-warmed at 65° in step (1), mixing thoroughly by pipetting up and down for 10 times, and then incubating the mixture at 65° for 5 minutes;
(5) placing the centrifuge tube on the magnetic separation rack and letting it stand for 1 minute until the liquid inside is clear, then carefully removing and discarding the supernatant;
(6) removing the centrifuge tube from magnetic stand and adding 1 ml of washing solution II pre-warmed at 65° in step (1), mixing thoroughly by pipetting up and down for 10 times, and then incubating the mixture at 65° for 5 minutes;
(7) placing the centrifuge tube on the magnetic separation rack and letting it stand for 1 minute until the liquid inside is clear, then carefully removing and discarding the supernatant;
(8) repeat step (6)-(7) for one more time;
(9) removing the centrifuge tube from magnetic stand and adding 1 ml of room temperature washing solution II, mixing thoroughly by pipetting up and down for 10 times, and then placing the centrifuge tube into rotary mixer and spinning it for 5 minutes;
(10) removing the centrifuge tube from magnetic stand and briefly centrifuging it at 600×g for 3 seconds to ensure that no beads are left on the tube wall or tube lid;
(11) placing the centrifuge tube on the magnetic separation rack and letting it stand until the liquid inside is clear, then carefully removing and discarding the supernatant as much as possible with a P10 pipette;
(12) keeping the centrifuge tube on the magnetic rack and adding 1 ml of washing solution III against the tube wall opposite to the beads, counting 30 seconds then carefully removing and discarding the supernatant as much as possible with the pipette;
(13) Letting the beads dry for 2 minutes, adding 22.5 μl nuclease-free water to resuspend magnetic beads by mixing them with the pipette up and down for 10 times, followed by heating the centrifuge tube at 98° for 10 minutes;
(14) after heating, vortex mixing the centrifuge tube and then briefly centrifuging it at 600×g for 3 seconds to ensure that no beads are left on the tube wall or tube lid;
(15) placing the centrifuge tube on the magnetic rack until the liquid inside is clear, immediately removing 20 μl supernatant containing hybridization-capture enriched DNA library sample for subsequent post-enrichment amplification.

Although the preferred embodiment of the present invention has been demonstrated in the foregoing description, it is understood that the present invention is not limited to the embodiment disclosed herein but is allowable for numerous modifications, without departing from the teachings of the present invention, by a skilled personnel. It is also understood that those modifications fall within the scope of the appended claims.

What is claimed is:

1. A washing solution for hybridization-enrichment-capture DNA sequencing libraries, wherein the washing solution includes the following three portions:
   a) washing solution I: 1×SSC, 0.1% SDS;
   b) washing solution II: 0.1×SSC, 0.1% SDS;
   c) washing solution III: 0.2×SSC, 10% SDS,
   wherein the washing solutions I, II and III each consist of saline sodium citrate (SSC) buffer and sodium dodecyl sulfate (SDS), and the washing solutions I, II and III are separately packaged.

2. A method for washing hybridization-enrichment-capture DNA sequencing libraries by using a washing solution including following three portions:
   a) washing solution I: 1×SSC, 0.1% SDS;
   b) washing solution II: 0.1×SSC, 0.1% SDS;
   c) washing solution III: 0.2×SSC, 10% SDS,
   wherein the SSC consists of 3M NaCl and 300 mM sodium citrate with a pH value of 7.0,
   the method comprising the following steps:
   (1) for each enrichment reaction, pre-incubating 1 ml washing solution I and 2 ml washing solution II at 65° C. for 30 minutes, and placing the other two portions under room temperature;
   (2) briefly centrifuging a hybridization reaction with biotin-labeled DNA probes captured by Invitrogen Dynabeads® M270 Streptavidin beads in a centrifuge tube at 600×g for 3 seconds, to ensure that there are no beads left on the tube wall or tube lid;
   (3) placing the centrifuge tube on a magnetic separation rack and letting it stand for 1 minute until the liquid inside is clear, then carefully removing and discarding the supernatant;
   (4) removing the centrifuge tube from magnetic stand and adding 1 ml of washing solution I pre-warmed at 65° C. in step (1), mixing thoroughly by pipetting up and down for 10 times, and then incubating the mixture at 65° C. for 5 minutes;
   (5) placing the centrifuge tube on the magnetic separation rack and letting it stand for 1 minute until the liquid inside is clear, then carefully removing and discarding the supernatant;
   (6) removing the centrifuge tube from magnetic stand and adding 1 ml of washing solution II pre-warmed at 65° C. in step (1), mixing thoroughly by pipetting up and down for 10 times, and then incubating the mixture at 65° C. for 5 minutes;
   (7) placing the centrifuge tube on the magnetic separation rack and letting it stand for 1 minute until the liquid inside is clear, then carefully removing and discarding the supernatant;
   (8) repeating step (6) to (7) for one more time;
   (9) removing the centrifuge tube from magnetic stand and adding 1 ml of room temperature washing solution II, mixing thoroughly by pipetting up and down for 10 times, and then placing the centrifuge tube into rotary mixer and spinning it for 5 minutes;
   (10) removing the centrifuge tube from magnetic stand and briefly centrifuging it at 600×g for 3 seconds to ensure that no beads are left on the tube wall or tube lid;
   (11) placing the centrifuge tube on the magnetic separation rack and letting it stand until the liquid inside is clear, then carefully removing and discarding the supernatant as much as possible with a P10 pipette;
   (12) keeping the centrifuge tube on the magnetic rack and adding 1 ml of washing solution III against the tube wall opposite to the beads, counting 30 seconds then carefully removing and discarding the supernatant as much as possible with the pipette;
   (13) letting the beads dry for 2 minutes, adding 22.5 μl nuclease-free water to resuspend magnetic beads by mixing them with the pipette up and down for 10 times, followed by heating the centrifuge tube at 98° C. for 10 minutes;
   (14) after heating, vortex mixing the centrifuge tube and then briefly centrifuging it at 600×g for 3 seconds to ensure that no beads are left on the tube wall or tube lid;
   (15) placing the centrifuge tube on the magnetic rack until the liquid inside is clear, immediately removing 20 μl supernatant containing hybridization-capture enriched DNA library sample for subsequent post-enrichment amplification.

* * * * *